United States Patent [19]
Olukotun et al.

[11] Patent Number: 5,622,985
[45] Date of Patent: Apr. 22, 1997

[54] METHOD FOR PREVENTING A SECOND HEART ATTACK EMPLOYING AN HMG COA REDUCTASE INHIBITOR

[75] Inventors: Adeoye Y. Olukotun, Hopewell, N.J.; John C. Alexander, Winnetka, Ill.

[73] Assignee: Bristol-Myers Squibb Company, Princeton, N.J.

[21] Appl. No.: 424,984

[22] Filed: Apr. 19, 1995

Related U.S. Application Data

[63] Continuation-in-part of Ser. No. 824,679, Jan. 23, 1992, abandoned, which is a continuation of Ser. No. 536,367, Jun. 11, 1990, abandoned.

[51] Int. Cl.$^6$ .......................... A61K 31/40; A61K 31/21
[52] U.S. Cl. .......................... 514/423; 514/510; 514/824
[58] Field of Search .................................. 514/423, 510, 514/824

[56] References Cited

U.S. PATENT DOCUMENTS

| | | | |
|---|---|---|---|
| 4,346,227 | 8/1982 | Terahara et al. | 560/119 |
| 4,920,123 | 4/1990 | Beyer | 514/255 |
| 5,008,284 | 4/1991 | Grover et al. | 514/424 |

FOREIGN PATENT DOCUMENTS

| | | |
|---|---|---|
| 0219782 | 4/1987 | European Pat. Off. . |
| 0461548A2 | 6/1991 | European Pat. Off. . |

OTHER PUBLICATIONS

Cecil, Textbook of Medicine, 16 Ed., pp. 239–242. (1983).
Schettler, G., "The role of diet and drugs in lowering serum cholesterol in the postmyocardial infarction patient," Cardiovasc. Drugs, Ther., 1989, 2/6 (795–799).
Glatter, T.R., "Hyperlipidemia. What is 'normal', who should be treated and how," Postgrad. Med., 1984, 76/6 (49–50).
Satler, L.F., et al, "Reduction in coronary heart disease: *Clinical and anatomical considerations,*" Clin. Cardiol., 1989, 12/8 (422–426).
Wilhelmsen, L., "Practical Guidelines for drug therapy after myocardial infarction," Drugs, 1989, 38/6 (1000–1007).
Yamamoto. A., et al., "Clinical features of familial hypercholeterolemia," Arteriosclerosis, Jan.–Feb. 1989, 9 (1 Suppl.) pp. 166–174.
Goldstein, J.L., et al, "The LDL receptor defect in familial hypercholesterolemia. Implications for pathogenesis and therapy,"0 Med. Clin North Am., 1982, 66/2 (335–362).
Osborne, J.A., et al, "Anti–ischemic Actions of Lovastatin (1) in Hypercholesterolemic Rabbits," Abstract of the 61st Scientific Sessions. (1989).
Tsujita, Y. "A Potent HMG–CoA Reductase Inhibitor, Pravastatin Sodium–Tissue–Selective Inhibition of Cholesterolgenesis and Preventive Effect on Atherosclerosis in WHHL Rabbits," J. Drug Dev. 1900:3(Suppl. 1), 155–159.

Maher, V.M., et al, "Analysis of Evidence from Cholesterol–Lowering and Regression Trials," J. Drug Dev. 1990:3 (Suppl. 1) 199–203.
Lewis, B. "On lowering lipids in the post–infarction patient," Journal of Internal Medicine 1991; 29:483–488.
"A Coronary Primary Prevention Study of Scottish Men Aged 45–64 Years: Trial Design," J. Clin Epidemiol vol. 45, No. 8 pp. 849–860, 1992.
Sacks, F.M., "Desirable Serum Total Cholesterol With Low HDL Cholesterol Levels," *Circulation*, vol. 86, No. 4, Oct. 1992, pp. 1341–1344.
Sacks, F.M., et al, "Effect on coronary atherosclerosis of decrease in plasma cholesterol concentrations in normocholesterolaemic patients", *The Lancet*, vol. 344, Oct. 1994, pp. 1182–1186.
Goldman, L., et al, "Projected Cost–Effectiveness of Lovastatin for Cholesterol Reduction," Clin. Res. (36, No. 3, 337A, 1988).
Sacks, F.M. et al, "Rationale and Design of a Secondary PreventionTrial of Lowering Normal Plasma cholesterol Levels After Acute Myocardial . . . Recurrent Events Trial (CARE)" , Am. J. Card. vol. 68, Dec. 1, 1991, pp. 1436–1446.
Fuster, V., et al, "Atherosclerotic Plaque Rupture and Thrombosis," Suppl. II, Circulation, vol. 82, No. 3, Sep. 1990, II–47–II59.
Crouse, J.R., et al, "Pravastatin, Lipids and Atherosclerosis in the Carotid Arteries: Design Features of a Clinical Trial with Carotid Atheroscelosis Outcome," Controlled Clinical Trails 13:495–506 (1992).
Edelman, S., et al., "Hyperkalemia During Treatment with HMG–CoA Reductase Inhibitor," New Engl. J. of Med., vol. 320, No. 18, May 4, 1989, pp. 1219–1220.
Pitt, B., et al, "design and Recruitment in the United States of a Multicenter Quantitative Angiographic Trial of Pravastatin to Limit Atherosclerosis in the Coronary Arteries" (PLAC I), Amer. J. Card., vol. 72, Jul. 1, 1993, pp. 31–35.
"Effects of Pravastatin in Patients with Serum Total Cholesterol Levels from 5.2 to 7.8 mmol/liter (200 to 30 mg/dl) Plus Two Additional Atherosclerotic Risk Factors," Am. J. Card., Nov. 1, 1993, pp. 1031–1037.
Pearson, T.A., et al, "The Rapid Reduction in Cardiac Events with Lipid–Lowering Therapy: Mechanisms and Implications," Am. J. Card., vol. 72, Nov. 1, 1993, pp. 1072–1073.

*Primary Examiner*—Kimberly Jordan
*Attorney, Agent, or Firm*—Burton Rodney

[57] ABSTRACT

A method is provided for preventing or reducing the risk of a second heart attack in a patient having a substantially normal serum cholesterol level by administering an HMG CoA reductase inhibitor such as pravastatin, alone or in combination with an ACE inhibitor.

19 Claims, No Drawings

METHOD FOR PREVENTING A SECOND HEART ATTACK EMPLOYING AN HMG COA REDUCTASE INHIBITOR

REFERENCE TO OTHER APPLICATIONS

This is a continuation-in-part of application Ser. No. 824,679 filed Jan. 23, 1992 now abandoned, which is a continuation of application Ser. No. 536,367 filed Jun. 11, 1990, now abandoned.

FIELD OF THE INVENTION

The present invention relates to a method for preventing or reducing the risk of a second heart attack in a patient having a substantially normal cholesterol level by administering an HMG CoA reductase inhibitor, such as pravastatin, alone or in combination with an ACE inhibitor.

BACKGROUND OF THE INVENTION

It is well established that lipid disorders are important factors in the development of coronary heart disease (CHD), Schettler, G., "The role of diet and drugs in lowering serum cholesterol in the postmyocardial infarction patient," Cardiovasc. Drugs Ther., 1989, 2/6 (795–799).

Glatter, T. R., "Hyperlipidemia. What is 'normal', who should be treated and how," Postgrad. Med., 1984, 76/6 (49–59), states that "As the coronary primary Prevention Trial has recently shown, a 1% reduction in cholesterol level produces a 2% reduction in risk of myocardial infarction."

Goldstein, J. L., et al, "The LDL receptor defect in familial hypercholesterolemia. Implications for pathogenesis and therapy," Med. Clin. North Am., 1982, 66/2 (335–362) indicate that "familial hypercholesterolemia was the first genetic disorder recognized to cause myocardial infarction. To this day, it remains the outstanding example of a singel gene mutation that causes both hypercholesterolemia and coronary atherosclerosis."

Satler, L. F., et al, "Reduction in coronary heart disease: Clinical and anatomical considerations," Clin. cardiol., 1989, 12/8 (422–426) disclose that "the higher the total plasma cholesterol and low density lipoprotein cholesterol (LDL-C), the greater the risk that coronary artery disease will develop. Recently, clinical trials including the Coronary Drug Project, the Lipid Research Clinics Coronary Primary Prevention Trial (LRC-CPPT), and the Helsinki Heart Study provided evidence that lowering cholesterol reduces the frequency of fatal and nonfatal coronary events." In addition, Satler et al disclose that other studies "demonstrated that lowering of cholesterol was associated with a decreased incidence of progression of coronary disease, as well as with the potential for reduction in the atherosclerotic plaque."

Wilhelmsen, L., "Practical guidelines for drug therapy after myocardial infarction," Drugs, 1989, 38/6 (1000–1007) discloses that it is advisable to correct blood.lipid disturbances in effective management of the postinfarction patient.

Yamamoto, A. et al, "Clinical features of familial hypercholesterolemia," Arteriosclerosis, January–February 1989, 9 (1 Suppl.) p I66-74, disclose that "in addition to the low density lipoprotein (LDL) cholesterol level, higher triglyceride and lower high density lipoprotein (HDL) cholesterol levels correlate with an increased risk of ischemic heart diseases."

There are several classes of compounds which have serum cholesterol lowering properties. Some of these compounds are inhibitors of the enzyme HMG CoA reductase which is essential in the production of cholesterol, such as mevastatin (disclosed in U.S. Pat. No. 3,983,140), lovastatin also referred to as mevinolin (disclosed in U.S. Pat. No. 4,231,938), pravastatin (disclosed in U.S. Pat. No. 4,346,227) and velostatin also referred to as synvinolin (disclosed in U.S. Pat. Nos. 4,448,784 and 4,450,171).

Other compounds which lower serum cholesterol may do so by an entirely different mechanism than the HMG CoA reductase inhibitors. For example, serum cholesterol may be lowered through the use of bile acid sequistrants such as cholestyramine, colestipol, DEAE-Sephadex and poly(diallylmethylamine) derivatives (such as disclosed in U.S. Pat. Nos. 4,759,923 and 4,027,009) or through the use of antihyperlipoproteinemics such as probucol and gemfibrozil which apparently lower serum "low density lipoproteins" (LDL) and/or converts LDL into high density lipoproteins (HDL).

Angiotension-converting enzyme inhibitors (ACE inhibitors) such as captopril and enalapril and known antihypertensive agents and, in addition, are known for their cardioprotective effects and for treating congestive heart failure.

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens dislcoses that ACE inhibition potentiates the action of bradykinin (a strong stimulator of prostacyclin release from endothelial cells) by inhibiting its degradation and ACE inhibitors, consequently, have an inhibitory effect on platelet aggregation.

Cecil, Textbook of Medicine, 16 Ed., pp 239 to 241, indicates at page 240 that blood pressure is an accelerator of atherosclerosis.

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-phenylbutyl)phosphinyl]-oxy]-1-oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

DESCRIPTION OF THE INVENTION

In accordance with the present invention, a method is provided for preventing onset of or reducing risk of a second heart attack in a mammalian species having a substantially normal serum cholesterol level, wherein a therapeutically effective amount of an HMG CoA reductase inhibitor, alone or in combination with an ACE inhibitor, is administered to a mammalian species having a substantially normal serum cholesterol level systemically, such as orally or parenterally.

In preferred embodiments where the patient to be treated in accordance with the present invention is normotensive, the angiotensin converting enzyme inhibitor, where employed, will preferably be administered in amounts below that required to cause hemodynamic effects, that is below that required to cause a reduction in blood pressure.

The combination of the HMG CoA reductase inhibitor and ACE inhibitor will be employed in a weight ratio to each other of within the range of from about 0.001:1 to about 1000:1 and preferably from about 0.05:1 to about 100:1.

The HMG CoA reductase inhibitor, alone or in combination with the ACE inhibitor will be administered as soon as possible after the initial myocardial infarction.

The term "substantially normal serum cholesterol level(s)" refers to a total cholesterol (TC) of less than 200 mg/dl, and preferably less than 190 mg/dl.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, velostatin (synvinolin) and related compounds as disclosed in U.S. Pat. Nos. 4,448,784 and 4,450,171, with lovastatin, pravastatin or velostatin being preferred. Other HMG CoA reductase inhibitors which may be employed herein include, but are not limited to, fluindostatin (Sandoz XU-62-320), pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]-pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Pat. No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydro-naphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837 which compounds have the moiety

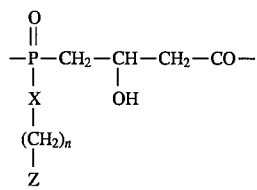

wherein X is —O— or —NH—, n is 1 or 2 and Z is a hydrophobic anchor.

Examples of such compounds include (S)-4-[[[4'-fluoro-3,3',5-trimethyl[1,1'-biphenyl]-2-yl]-methoxy]methoxyphosphinyl]-3-hydroxy-butanoic acid, methyl ester or its monolithium salt, (S)-4-[[[4'-fluoro-3,3',5-trimethyl[1,1'-biphenyl]-2-yl]methoxy]hydroxyphosphinyl]-3-hydroxybutanoic acid, dilithium salt, (3S)-4-[[[4'-fluoro-3,3',5-trimethyl[1,1'-biphenyl]-2-yl] methoxy]methylphosphinyl]-3-hydroxybutanoic acid, monolithium salt, (S)-4-[[[2,4-dichloro-6-[(4-fluorophenyl)-methoxy]phenyl] methoxy]methoxyphosphinyl]-3-hydroxybutanoic acid, monolithium salt, (3S)-4-[[[2,4-dichloro-6-[(4-fluorophenyl)-methoxy]phenyl]methoxy]hydroxyphosphinyl]-3-hydroxybutanoic acid, dilithium salt, (3S)-4-[[2,4-dichloro-6-[(4-fluorophenyl)-methoxy]phenyl] methoxy]methylphosphinyl]-3-hydroxybutanoic acid, or its methyl ester, and (S)-4-[[[[4'-fluoro-3,3',5-trimethyl[1,1'-biphenyl-2-yl]methyl]amino]methoxyphosphinyl]-3-hydroxybutanoic aicd, monolithium salt.

Another class of HMG CoA reductase inhibitors suitable for use herein include phosphinic acid compounds disclosed in GB 2205838, which compounds have the moiety

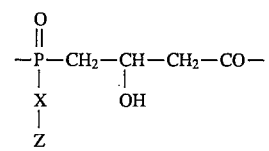

wherein X is —CH$_2$— —CH$_2$—CH$_2$—, —CH═CH—, —CH$_2$CH$_2$CH$_2$—, —C≡C— or —CH$_2$O—, where O is linked to Z, and Z is a hydrophobic anchor.

Examples of such compounds include (S)-4-[[[1-(4-fluorophenyl)-3-(1-methylethyl )-1H-indol-2-yl]ethynyl]hydroxyphosphinyl]-3-hydroxyfutanoic acid, or its sodium salt (SQ 33,600) (preferred) or its dilithium salt;

(S)-4-[[(E)-2-[4'-fluoro-3,3',5'-trimethyl[1,1'-biphenyl]-2-yl]ethenyl]hydroxyphosphinyl]-3hydroxybutanoic acid or its dilithium salt;

(S)-4-[[2-[4'-fluoro-3,3',5'-trimethyl-[1,1'-biphenyl]-2-yl]ethyl]hydroxyphosphinyl]-3-hydroxybutanoic acid, methyl ester or mono- or di-alkali metal salts thereof;

(S)-4-[[[4'-fluoro-3,3',5'-trimethyl-[1,1'-biphenyl]-2-yl]ethynyl]methoxyphosphinyl]-3-hydroxybutanoic acid or the methyl ester thereof;

(5Z)-4-[[2-[4'-fluoro-3,3',5'-trimethyl-[1,1'-biphenyl]-2-yl]ethenyl]hydroxyphosphinyl]3-hydroxybutanoic methyl esters thereof; acid, methyl esters thereof;

(S)-4-[[2-[3-(4-fluorophenyl)-1-(1-methyl-ethyl)-1H-indol-2-yl]ethyl]methoxyphosphinyl]-3-hydroxybutanoic acid, methyl esters;

(S)-4-[[2-[[1,1'-biphenyl]-2-yl]ethyl]-methoxyphosphinyl-3-hydroxybutanoic acid, methyl ester;

(S)-4-[[2-[4'-fluoro-3,3',5'-trimethyl-[1,1'-biphenyl]-2-yl]ethyl]hydroxyphosphinyl]-3-hydroxybutanoic acid, dilithium salt;

(S)-4-[[2-[4'-fluoro-3,3',5'-trimethyl-[1,1'-biphenyl]-2-yl]ethynyl]hydroxyphosphinyl]-3-hydroxybutanoic acid, dilithium salt;

(SZ)-4-[[2-[4'-fluoro-3,3',5'-trimethyl-[1,1'-biphenyl]-2-yl]ethenyl]hydroxyphosphinyl]-3-hydroxybutanoic acid, dilithium salt;

(S)-4-[[2-[3-(4-fluorophenyl)-1-(1-methylethyl-)-1H-indol-2-yl]ethyl]hydroxyphosphinyl]-3-hydroxybutanoic acid, dilithium salt;

(S)-4-[[2-[(1,1'-biphenyl]-2-yl]ethyl]-hydroxyphosphinyl]-3-butanoic acid, dilithium salt;

(S)-4-(hydroxymethoxyphosphinyl)-3-[[(1,1-dimethylethyl) diphenylsilyl]oxy]butanoic acid, methyl ester, or its dicyclohexylamine (1:1) salt;

(S)-4-[[2-[1-(4-fluorophenyl)-3-(1-methy-lethyl)-1-indol-2-yl]ethynyl]hydroxyphosphinyl]-3-hydroxybutanoic acid or its dilithium salt or disodium salt or methyl ester thereof;

(E)-4-[[2-[3-(4-fluorophenyl)-1-(1-methyl-ethyl)-1H-indol-2-yl]ethenyl]hydroxyphosphinyl]-3-hydroxybutanoic acid or its dilithium salt or methyl ester thereof;

4-[[2-[4'-fluoro-3,3',5-trimethyl[1,1'-biphenyl]-2-yl]ethyl]hydroxyphosphinyl]-3-hydroxybutanoic acid or its dilithium salt or methyl ester thereof;

(E)-4-[[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;

(S)-4-[[[2,4-dimethyl-6-[(4-fluorophenyl)-methoxy]phenyl]ethyl]hydroxyphosphinyl]-3-hydroxybutanoic acid or its dilithium salt or methyl ester thereof;

(S)-4-[[[2,4-dimethyl-6-[(4-fluorophenyl)-methoxy]phenyl]ethynyl]hydroxyphosphinyl]-3-hydroxybutanoic acid or its dilithium salt or methyl ester thereof;

(S)-4-[[2-[3,5-dimethyl[1,1'-biphenyl)-2-yl]ethyl)hydroxyphosphinyl]-3-hydroxybutanoic acid or its dilithium salt or methyl ester thereof;

(S)-4-[[2-[4'-fluoro-3,5-dimethyl[1,1'-biphenyl]-2-yl]ethyl]hydroxyphosphinyl]-3-hydroxybutanoic acid or its dilithium salt or methyl ester thereof;

(S)-4-[[2-[[1,1'-biphenyl]-2-yl]ethynyl]-hydroxyphosphinyl]-3-hydroxybutanoic acid or its dilithium salt or methyl ester thereof;

(S)-4-[[2-(5-(4-fluorophenyl)-3-(1-methyl-ethyl)-1-phenyl-1H-pyrazol-4-yl]ethynyl]methoxy-phosphinyl]-3-hydroxybutanoic acid, methyl ester;

(S)-4-[[2-[1-(4-fluorophenyl)-3-(1-methyl-ethyl)-1H-indol-2-yl]ethyl]hydroxyphosphinyl]-3-hydroxybutanoic acid or its dilithium salt or methyl ester thereof;

(S)-4-[[2-[5-(4-fluorophenyl)-3-(1-methyl-ethyl)-1-phenyl-1H-pyrazol-4-yl]ethynyl]hydroxy-phosphinyl]-3-hydroxybutanoic acid, dilithium salt;

(E)-4-[[2-[5-(4-fluorophenyl)-3-(1-methyl-ethyl)-1-phenyl-1H-pyrazol-4-yl]ethenyl]methoxy-phosphinyl]-3-hydroxybutanoic acid, methyl ester;

(E)-4-[[2-[5-(4-fluorophenyl)-3-(1-methyl-ethyl)-1-phenyl-1H-pyrazol-4-yl]ethenyl]hydroxy-phosphinyl]-3-hydroxybutanoic acid, dilithium salt;

(S)-4-[[2-[5-(4-fluorophenyl)-3-(1-methyl-ethyl)-1-phenyl-1H-pyrazol-4-yl]ethyl]methoxy-phosphinyl]-3-hydroxybutanoic acid, methyl ester;

(S)-4-[[2-[5-(4-fluorophenyl)-3-(1-methyl-ethyl)-1-phenyl-1H-pyrazol-4-yl]ethyl]methoxy-phosphinyl]-3-hydroxybutanoic acid, dilithium salt;

(S)-4-[[2-[3-(4-fluorophenyl)-5-(1-methyl-ethyl)-1-phenyl-1H-pyrazol-4-yl]ethyl]hydroxy-phosphinyl]-3-hydroxybutanoic acid, methyl ester;

(S)-4-[[2-[3-(4-fluorophenyl)-5-(1-methyl-ethyl)-1-phenyl-1H-pyrazol-4-yl]ethyl]methoxy-phosphinyl]-3-hydroxybutanoic acid, dilithium salt;

(S)-4-[[2-[3-(4-fluorophenyl)-5-(1-methylethyl)-1-phenyl-1H-pyrazol-4-yl]ethynyl]methoxy-phosphinyl]-3-hydroxybutanoic acid, methyl ester;

(S)-4-[[2-[3-(4-fluorophenyl)-5-(1-methylethyl)-1-phenyl-1H-pyrazol-4-yl]ethynyl]hydroxyphosphinyl]-3-hydroxybutanoic acid, dilithium salt;

(S)-4-[[[4-(4-fluorophenyl)-1-(1-methyl-ethyl)-3-phenyl-1H-pyrazol-5-yl]ethynyl]methoxy-phosphinyl]-3-hydroxybutanolc acid, methyl ester;

(S)-4-[[[4-(4-fluorophenyl)-1-(1-methyl-ethyl)-3-phenyl-1H-pyrazol-5-yl]ethynyl]hydroxy-phosphinyl]-3-hydroxybutanoic acid, dilithium salt;

(S)-4-[[2-[4-(4-fluorophenyl)-1-(1-methyl-ethyl)-3-phenyl-1H-pyrazol-5-yl]ethyl]methoxy-phosphinyl]-3-hydroxybutanoic acid, methyl ester;

(S)-4-[[2-[4-(4-fluorophenyl)-1-(1-methyl-ethyl)-3-phenyl-1H-pyrazol-5-yl]ethyl]hydroxy-phosphinyl]-3-hydroxybutanoic acid, dilithium salt;

(S)-4-[[[1-(4-fluorophenyl)-4-(1-methyl-ethyl)-2-phenyl-1H-imidazole-5-yl]ethynyl]methoxy-phosphinyl]-3-hydroxybutanoc acid, methyl ester;

(S)-4-[[[1-(4-fluorophenyl)-4-(1-methyl-ethyl)-2-phenyl-1H-imidazol-5-yl]ethynyl]methoxy-phosphinyl]-3-hydroxybutanoic acid, methyl ester;

(S)-4-[[2-[1-(4-fluorophenyl)-4-(1-methyl-ethyl)-2-phenyl-1H-imidazol-5-yl]ethyl]methoxy-phosphinyl]-3-hydroxybutanoc acid, methyl ester;

(S)-4-[[2-[1-(4-fluorophenyl)-4-(1-methyl-ethyl)-2-phenyl-1H-imidazol-5-yl]ethyl]hydroxy-phosphinyl]-3-hydroxybutanoic acid, dilithium salt;

(S)-4-[[[2-(cyclohexylmethyl)-4,6-dimethyl-phenyl]ethynyl]hydroxy-phosphinyl]-3-hydroxybutanoic acid or its dilithium salt or methyl ester thereof;

4-[[2-[2-(cyclohexylmethyl)-4,6-dimethylphenyl]ethenyl]hydroxy-phosphinyl]-3-hydroxybutanoic acid or its dilithium salt or methyl ester thereof;

(S)-4-[[2-[2-(cyclohexylmethyl)-4,6-dimethyl-phenyl]ethyl]hydroxyphosphinyl]-3-hydroxybutanoic acid or its dilithium salt or methyl ester thereof;

4-[[[[4'-fluoro-3,3 ',5-trimethyl [1,1'-biphenyl]-2-yl]oxy]methyl]hydroxyphosphinyl]-3-hydroxybutanoic acid or its dilithium salt or methyl ester thereof;

4-[[[4'-fluoro-3,3',5-trimethyl [1,1'-biphenyl]-2-yl]methyl]hydroxyphosphinyl]-3-hydroxy-butanoic acid or its dilithium salt or methyl ester thereof;

(S)-4-[[[1-(4-fluorophenyl)-3-methyl-2-naphthalenyl]ethynyl]hydroxyphosphinyl]-3-hydroxy-butanoic acid or its dilithium salt or methyl ester thereof;

(E)-4-[[2-[1-(4-fluorophenyl)-3-methyl-2-naphthalenyl]ethenyl]hydroxyphosphinyl]-3-hydroxy-butanoic acid or its dilithium salt or methyl ester thereof;

(S)-4-[[2-[1-(4-fluorophenyl)-3-methyl-2-naphthalenyl]ethyl]hydroxyphosphinyl]-3-hydroxy-butanoic acid or its dilithium salt or methyl ester thereof;

4-[[3-[4'-fluoro-3,3',5-trimethyl[1,1'-biphenyl]-2-yl]propyl]methoxyphosphinyl]-3-hydroxy-butanoic acid, methyl ester;

4-[[3-[4'-fluoro-3,3',5-trimethyl[1,1'-biphenyl]-2-yl]propyl]hydroxyphosphinyl]-3-hydroxybutanoic acid, dilithium salt;

[1S-[1α(R*),2α,4αβ,8β,8aα]]-4-[[2-[8-(2,2-dimethyl-1-oxobutoxy)decahydro-2-methyl-1-naphthalenyl]ethyl]methoxyphosphinyl]-3-hydroxy-butanoic acid, methyl ester;

[1S-[1α(R*),2α,4aβ,8β,8β]]-4-[[2-[8-(2,2-dimethyl-1-oxobutoxy)decahydro-2-methyl-1-naphthalenyl]ethyl]hydroxyphosphinyl]-3-hydroxybutanoic acid, dilithium salt;

(S)-4-[[[3'-(4-fluorophenyl)spiro]cyclopentane-1,1'-[1H]indene]-2-yl]ethynyl]methoxyphosphinyl]-3-hydroxybutanoic acid, methyl ester; and (S)-4-[[[3'-(4-fluorophenyl)spiro]cyclopentane-1,1'-[1H]indene]-2-yl]ethynyl]hydroxyphosphinyl]-3-hydroxybutanoic acid, dilithium salt.

Preferred are pravastatin or SQ 33,600.

The above-mentioned U.S. patents are incorporated herein by reference.

The angiotensin converting enzyme inhibitor which may be employed herein preferably includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

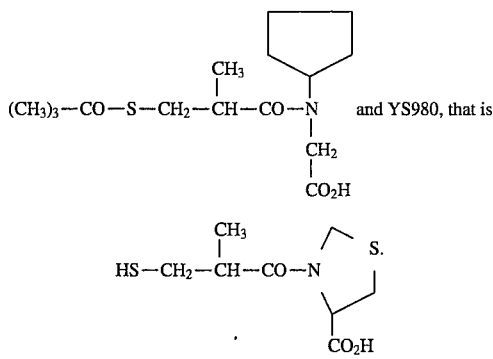

and YS980, that is

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyl]oxy]-1-oxohexyl]-L-proline (SQ 29,852 or ceranapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepinne-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacolo 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4-tetrahydro-6,7-dimethoxy-3-isoquinoline-carboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives and most preferred are such ACE inhibitors which include a mercapto group.

The above-mentioned U.S. patents are incorporated herein by reference.

In carrying out the method of the present invention, the HMG CoA reductase inhibitor alone or in combination with the ACE inhibitor may be administered to mammalian species having substantially normal serum cholesterol levels, such as dogs, cats, humans, etc., and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the FIMG CoA reductase inhibitor in dosages employed, for example, for pravastatin, lovastatin and simvastatin as indicated in the Physician's Desk Reference, such as in an amount within the range of from about 1 to 2000 mg, and preferably from about 4 to about 200 mg.

A preferred oral dosage form, such as tablets or capsules, will contain the HMG CoA reductase inhibitor in an amount of from about 0.5 to about 100 mg, preferably from about 5 to about 80 mg, and more preferably from about 10 to about 40 mg.

With regard to the ACE inhibitor, for oral administration, a satisfactory result may be obtained employing the ACE inhibitor in an amount within the range of from about 0.01 mg/kg to about 100 mg/kg and preferably from about 0.1 mg/kg to about 5 mg/kg.

A preferred oral dosage form, such as tablets or capsules, will contain the ACE inhibitor in an amount of from about 0.1 to about 500 mg, preferably from about 2 to about 50 mg, and more preferably from about 10 to about 25 mg.

For parenteral administration, the ACE inhibitor will be employed in an amount within the range of from about 0.005 mg/kg to about 10 mg/kg and preferably from about 0.005 mg/kg to about 2 mg/kg.

The HMG CoA reductase inhibitor and ACE inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

The compositions described above may be administered in the dosage forms as described above in single or divided doses of one to four times daily. It may be advisable to start a patient on a low dose combination and work up gradually to a high dose combination.

Liquid formulations can also be prepared by dissolving or suspending one or the combination of the active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of HMG CoA reductase inhibitor and ACE inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described: above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for a second heart attack remains or the symptoms continue. Sustained release forms of such formulations which may provide such amounts biweekly, weekly, monthly and the like may also be employed. A dosing period of at least one to two weeks are required to achieve minimal benefit.

The following Examples represent preferred embodiments of the invention.

EXAMPLE 1

A pravastatin formulation in the form of tablets having the following composition was prepared as described below.

| Ingredient | Parts by Weight |
| --- | --- |
| Pravastatin | 7 |
| Lactose | 67 |
| Microcrystalline cellulose | 20 |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magesium stearate was added and mixing was continued for 1 to 3 minutes.

The resulting homogeneous mixture was then compressed into tablets each containing 5 mg, 10 m, 20 mg or 40 mg pravastatin which may be used in preventing or reducing risk of a second heart attack. in a patient having a substantially normal serum cholesterol level.

EXAMPLE 2

Pravastatin tablets are prepared employing conventional pharmaceutical techniques containing 20 mg pravastatin and inert ingredients employed in lovastatin tablets, namely cellulose, color, lactose, magnesium stearate and starch and butylated hydroxy-anisole as a preservative as described in the 1990 PDR.

The pravastatin tablets may be employed to prevent or reduce risk of a second heart attack in a patient having a substantially normal serum cholesterol level in accordance with the present invention.

EXAMPLE 3

Tablets of the following compositions are prepared as described below.

| Ingredient | Weight (mg) |
| --- | --- |
| SQ 33,600 | 100 mg |
| Avicel | 112.5 mg |
| Lactose | 113 mg |
| Cornstarch | 17.5 mg |
| Stearic Acid | 7 mg |
|  | 350 mg |

The tablets are prepared from sufficient bulk quantities by slugging the SQ 33,600, Avicel, and a portion of the stearic acid. The slugs are ground and passed through a #2 screen and then mixed with the lactose, cornstarch, and the remainder of stearic acid. The mixture is compressed into 350 mg capsule shaped tablets in a tablet press. The tablets are scored for dividing in half.

The so-formed tablets may be administered in accordance with the teachings of the present invention to prevent or reduce risk of a second heart attack in a patient having a substantially normal serum cholesterol level.

EXAMPLE 4

Lovastatin tablets are prepared employing conventional pharmaceutical techniques containing 20 mg lovastatin, cellulose, color, lactose, magnesium stearate and starch and butylated hydroxyanisole as a preservative as described in the 1990 PDR.

The lovastatin tablets may be employed to prevent or reduce risk of second heart attack in a patient having a substantially normal serum cholesterol level in accordance with the present invention.

EXAMPLE 5

A pravastatin formulation in the form of tablets is prepared as described in Example 1.

A captopril formulation suitable for oral administration together with pravastatin is prepared as described below.

1000 tablets each containing 25 mg of 1-[(2S)-3-mercapto-2-methylpropionyl]-L-proline were produced from the following ingredients.

| | |
|---|---|
| 1-[(2S)-3-Mercapto-2-methylpropionyl]-L-proline (captopril) | 25 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 25 mg of active ingredient.

The pravastatin tablets and captopril tablets may be administered as a combination in accordance with the teachings of the present invention to prevent or reduce the risk of a second heart attack in a patient having a substantially normal serum cholesterol level. In addition, the pravastatin and captopril tablets may be ground up into powders and used together in a single capsule.

EXAMPLE 6

Pravastatin tablets are prepared as described in Example 2.

The pravastatin tablets may be employed in combination with enalapril tablets containing 20 mg enalapril and inactive ingredients as described in the 1990 PDR, in separate or combined dosage forms to prevent or reduce the risk of a second heart attack in a patient having a substantially normal serum cholesterol level in accordance with the present invention.

EXAMPLE 7

Tablets containing SQ33,600 prepared as described in Example 3 may be administered together with 25 mg captopril tablets to prevent or reduce risk of a second heart attack in a patient having a substantially normal serum cholesterol level.

EXAMPLE 8

Lovastatin tablets are prepared employing conventional pharmaceutical techniques containing 20 mg lovastatin, cellulose, color, lactose, magnesium stearate and starch and butylated hydroxyanisole as a preservative as described in the 1990 PDR.

The lovastatin tablets may be employed alone or in combination with the captopril tablets (described in Example 5) or ceranapril tablets in separate or combined dosage forms to prevent or reduce risk of a second heart attack in a patient having a substantially normal serum cholesterol level in accordance with the present invention.

What is claimed is:

1. A method for preventing or reducing the risk of a second heart attack in a mammalian species having a substantially normal serum cholesterol level, which comprises administering to a mammalian species having a substantially normal serum cholesterol level in need of such treatment a therapeutically effective amount of an inhibitor of the enzyme 3-hydroxy-3-methylglutaryl coenzyme A (HMG CoA) reductase.

2. The method as defined in claim 1 wherein said inhibitor of the enzyme HMG CoA reductase is mevastatin, lovastatin, pravastatin or velostatin.

3. The method as defined in claim 1 wherein said inhibitor of the enzyme HMG CoA reductase is a pyrazole analog of a mevalonolactone, an indene analog of mevalonolactone, a 3-carboxy-2-hydroxypropane-phosphinic acid derivative, a 6-[2-(substituted-pyrrol-1-yl)-alkyl]pyran-2-one, an imidazole analog of mevalonolactone, a naphthyl analog of mevalonolactone, an octahydro-naphthalene, fluindostatin, a keto analog of lovastatin or a 2,3-di-substituted pyrrole, furan or thiophene.

4. The method as defined in claim 1 wherein said HMG CoA reductase inhibitor is pravastatin.

5. The method as defined in claim 1 wherein said HMG CoA reductase inhibitor is administered in single or divided doses of from about 0.5 to about 100 mg/one to four times daily.

6. The method as defined in claim 1 wherein said HMG CoA reductase inhibitor is administered in single or divided doses of from about 5 to about 80 mg/one to four times daily.

7. A method for preventing or reducing the risk of a second heart attack in a mammalian species having a substantially normal serum cholesterol level, which comprises administering to a mammalian species having a substantially normal serum cholesterol level in need of such treatment a therapeutically effective amount of an HMG CoA reductase inhibitor in combination with a therapeutically effective amount of an angiotensin converting enzyme (ACE) inhibitor.

8. The method as defined in claim 7 wherein the angiotensin converting enzyme inhibitor is captopril or fosinopril.

9. The method as defined in claim 7 wherein said angiotensin converting enzyme inhibitor includes a mercapto moiety and is a substituted proline derivative.

10. The method as defined in claim 7 wherein said angiotensin converting enzyme inhibitor is captopril, zofenopril, enalapril, ceranopril, fosinopril, lisinopril or fentiapril.

11. The method as defined in claim 7 wherein the angiotensin converting enzyme inhibitor is a phosphonate substituted amino or imino acid or salt thereof, a mercaptoacyl derivative of a substituted proline, a carboxyalkyl dipeptide, a phosphinylalkanoyl proline or a phosphonoamidate.

12. The method as defined in claim 7 wherein the HMG CoA reductase inhibitor is present in a weight ratio to the ACE inhibitor of within the range of from about 0.001:1 to about 1000:1.

13. The method as defined in claim 7 wherein the HMG CoA reductase inhibitor is pravastatin.

14. The method as defined in claim 7 wherein said angiotensin converting enzyme inhibitor is administered in single or divided doses of from about 0.1 to about 500 mg/one to four times daily.

15. The method as defined in claim 7 wherein the HMG CoA reductase inhibitor is pravastatin and the ACE inhibitor is captopril, fosinopril or ceranopril.

16. The method as defined in claim 7 wherein said angiotensin converting enzyme inhibitor is administered in single or divided doses of from about 2 to about 50 mg/one to four times daily.

17. The method as defined in claim 7 wherein the mammalian species treated is normotensive.

18. The method as defined in claim 17 wherein the ACE inhibitor is administered in an amount below that required to cause hemodynamic effects.

19. The method as defined in claim 7 wherein the HMG CoA reductase inhibitor is employed in an amount of within the range of from about 5 to about 80 mg and the ACE inhibitor is employed in an amount within the range of from about 2 to about 5 mg.

* * * * *